(12) United States Patent
Tachikawa et al.

(10) Patent No.: US 8,766,220 B2
(45) Date of Patent: Jul. 1, 2014

(54) CHARGED PARTICLE BEAM IRRADIATION APPARATUS

(71) Applicant: Sumitomo Heavy Industries, Ltd., Tokyo (JP)

(72) Inventors: Toshiki Tachikawa, Ehime (JP); Tsuyoshi Ogasawara, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/063,764

(22) Filed: Oct. 25, 2013

(65) Prior Publication Data
US 2014/0077098 A1    Mar. 20, 2014

Related U.S. Application Data

(63) Continuation of application No. PCT/JP2012/058231, filed on Mar. 28, 2012.

(30) Foreign Application Priority Data

Apr. 27, 2011 (JP) .................................. 2011-099461

(51) Int. Cl.
G21K 5/04 (2006.01)
(52) U.S. Cl.
CPC ........................................ G21K 5/04 (2013.01)
USPC ........................................................ 250/492.3
(58) Field of Classification Search
USPC .................................. 250/492.3; 378/65, 145
See application file for complete search history.

(56) References Cited

U.S. PATENT DOCUMENTS 8,536,548 B2 *   9/2013   Otani et al. ................. 250/492.3

FOREIGN PATENT DOCUMENTS

JP            07-255718 A      10/1995

* cited by examiner

Primary Examiner — Kiet T Nguyen
(74) Attorney, Agent, or Firm — Rader, Fishman & Grauer PLLC

(57) ABSTRACT

A charged particle beam irradiation apparatus includes: an irradiation section configured to irradiate an irradiated body with a charged particle beam; a multi-leaf collimator configured to set an irradiation range of the charged particle beam which is irradiated from the irradiation section; an imaging section that is provided so as to be able to advance and retreat with respect to an irradiation axis of the charged particle beam which is irradiated from the irradiation section, between the irradiation section and the multi-leaf collimator, and directly images an opening portion of the multi-leaf collimator; and a drive section configured to move the imaging section between an imaging position corresponding to an irradiation area which includes the irradiation axis of the charged particle beam and a retreated position away from the irradiation area.

4 Claims, 5 Drawing Sheets

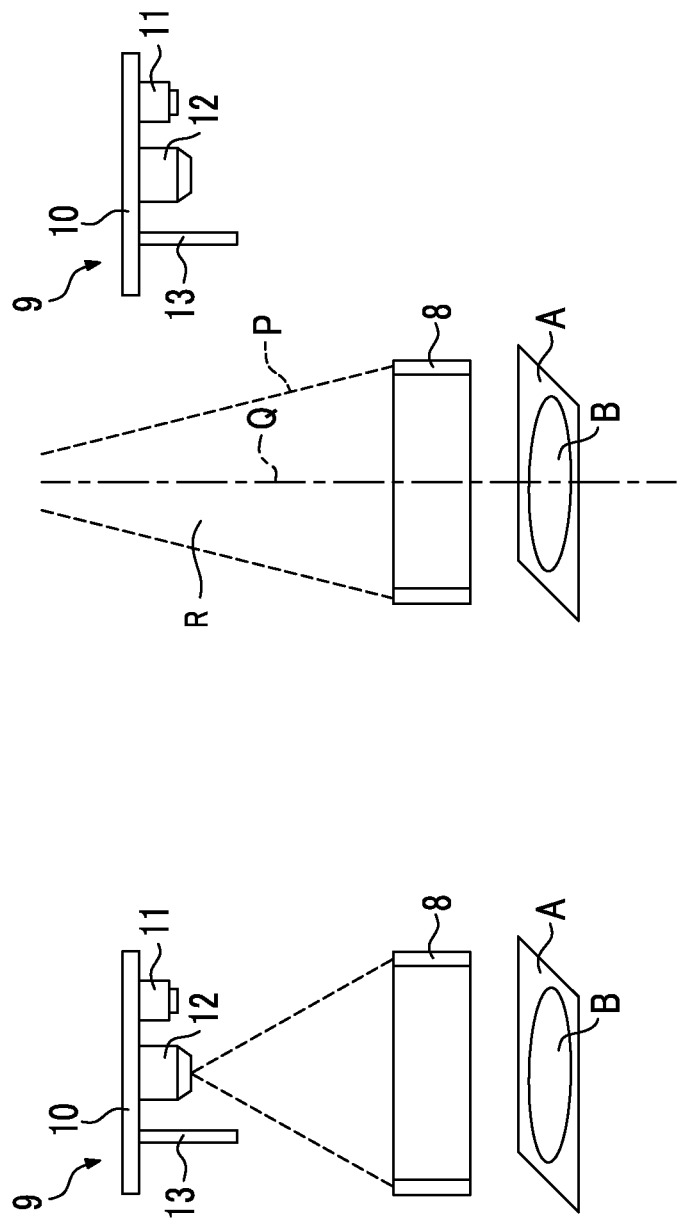

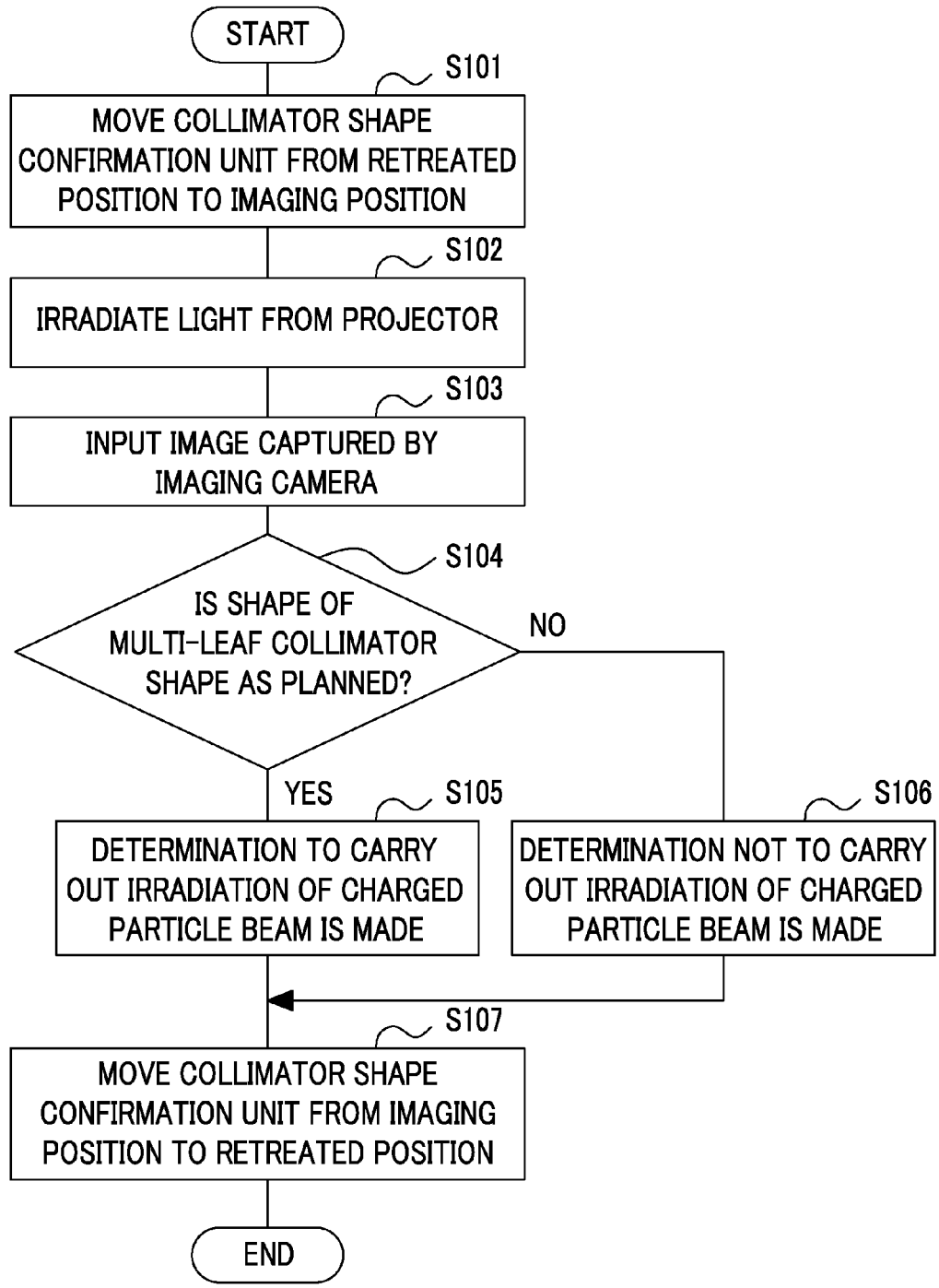

CHARGED PARTICLE BEAM IRRADIATION APPARATUS

INCORPORATION BY REFERENCE

Priority is claimed to Japanese Patent Application No. 2011-099461, filed Apr. 27, 2011, and International Patent Application No. PCT/JP2012/058231, the entire content of each of which is incorporated herein by reference.

BACKGROUND

1. Technical Field

The present invention relates to a charged particle beam irradiation apparatus that irradiates an irradiated body with a charged particle beam.

2. Description of the Related Art

A charged particle beam irradiation apparatus that irradiates a charged particle beam is used in a radiation therapy apparatus that performs cancer therapy by irradiating a tumor area of a patient with, for example, a proton beam. As such a radiation therapy apparatus, for example, a radiation therapy apparatus described in the related art is known. The radiation therapy apparatus described in the related art is provided with a radiation generation section which generates a radiation which is irradiated to the body surface of a tested object, a multi-leaf collimator which determines an irradiation field of the radiation irradiated from the radiation generation section, and a CCD camera which photographs the tested object through an opening portion of the multi-leaf collimator, and performs predetermined processing on the basis of a captured image obtained by the CCD camera.

SUMMARY

According to an embodiment of the present invention, there is provided a charged particle beam irradiation apparatus including: an irradiation section configured to irradiate an irradiated body with a charged particle beam; a multi-leaf collimator configured to set an irradiation range of the charged particle beam which is irradiated from the irradiation section; an imaging section that is provided so as to be able to advance and retreat with respect to an irradiation axis of the charged particle beam which is irradiated from the irradiation section, between the irradiation section and the multi-leaf collimator, and directly images an opening portion of the multi-leaf collimator; and a drive section configured to move the imaging section between an imaging position corresponding to an irradiation area which includes the irradiation axis of the charged particle beam and a retreated position away from the irradiation area.

BRIEF DESCRIPTION OF THE DRAWINGS

FIGS. 4A and 4B are schematic diagrams showing states where the collimator shape confirmation unit shown in FIG. 2 is at an imaging position and a retracted position.

FIG. 5 is a flowchart showing the details of the processing procedure which is executed by a controller shown in FIG. 3.

DETAILED DESCRIPTION

Figure 1:
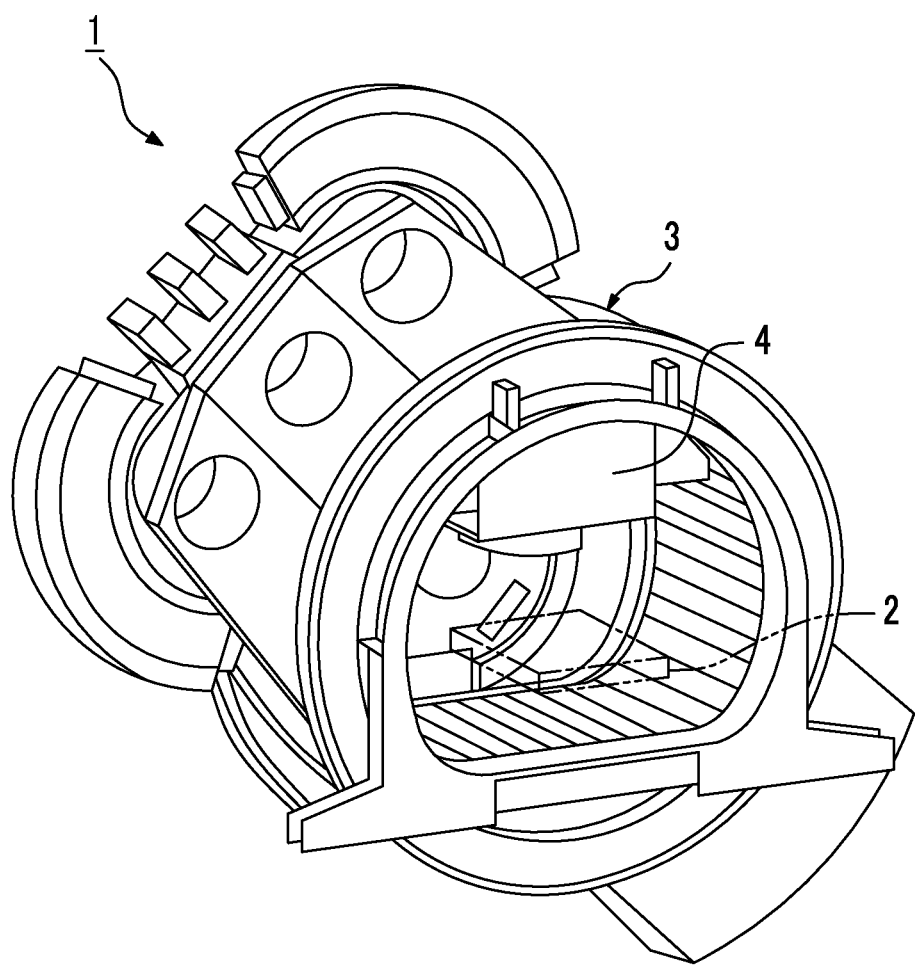
FIG. 1 is a perspective view showing a charged particle beam therapy apparatus provided with a charged particle beam irradiation apparatus according to an embodiment of the present invention.

In the related art, an installation position of a CCD camera is fixed and an opening portion of a multi-leaf collimator is imaged through two half mirrors by the CCD camera. For this reason, a captured image obtained by the CCD camera is sometimes distorted. Further, there is also a mounting error or the like of the two half mirrors. For this reason, a problem in that the captured image of the CCD camera is different from an actual image can arise. Accordingly, in order to confirm whether the shape of the opening portion of the multi-leaf collimator is shaped as planned, with an image, it is necessary to carry out complicated processing such as performing some sort of error correction processing on output image data of the CCD camera.

It is desirable to provide a charged particle beam irradiation apparatus in which it is possible to obtain a clear captured image of an opening portion of a multi-leaf collimator.

In the charged particle beam irradiation apparatus according to an embodiment of the present invention, before the charged particle beam is irradiated from the irradiation section to the irradiated body, the opening portion of the multi-leaf collimator is imaged by the imaging section and whether the shape of the opening portion of the multi-leaf collimator is a shape as planned is confirmed with an image. Usually, the imaging section is located at the retreated position away from the irradiation area that includes the irradiation axis of the charged particle beam which is irradiated from the irradiation section. When imaging by the imaging section is performed, the imaging section is moved from the retreated position to the imaging position corresponding to the irradiation area which includes the irradiation axis of the charged particle beam by the drive section. Then, the opening portion of the multi-leaf collimator is imaged by the imaging section at the imaging position. Due to making the imaging section be able to advance and retreat with respect to the irradiation axis of the charged particle beam which is irradiated from the irradiation section in this manner, it is not necessary to dispose a half mirror between the multi-leaf collimator and the imaging section unlike a case where the installation position of the imaging section is fixed, and therefore, it is possible to directly image the opening portion of the multi-leaf collimator. For this reason, a problem such as distortion occurring in the captured image of the imaging section is prevented. In this way, it is possible to obtain a clear captured image of the opening portion of the multi-leaf collimator.

Preferably, the imaging section is mounted on a mounting bracket that can advance and retreat with respect to the irradiation axis of the charged particle beam, the drive section moves the mounting bracket between the imaging position and the retreated position, and a shield wall for protecting the imaging section from the charged particle beam is provided closer to the side of the irradiation axis of the charged particle beam than the imaging section in the mounting bracket when the mounting bracket is at the retreated position. By providing the shield wall for protecting the imaging section from the charged particle beam in this manner, charged particle beam damage to the imaging section during the irradiation of the charged particle beam is suppressed.

In this case, preferably, a light source section configured to irradiate light to the opening portion of the multi-leaf collimator may be further mounted on the mounting bracket. By providing the light source section in this manner, in a state where the mounting bracket is at the imaging position, light is directly irradiated toward the opening portion of the multi-leaf collimator from the light source section, and therefore, when imaging the opening portion of the multi-leaf collimator by the imaging section, the opening portion of the multi-leaf collimator is illuminated. Accordingly, it is possible to obtain a clear captured image of the opening portion of the multi-leaf collimator.

It is preferable that the light source section be mounted on the mounting bracket so as to be located on the irradiation axis of the charged particle beam when the mounting bracket is at the imaging position. In the charged particle beam irradiation apparatus, there is a case where an irradiated body collimator is disposed below the multi-leaf collimator. The irradiated body collimator is made for each irradiated body and has an opening portion matching an irradiation target (an affected area) of the irradiated body. Furthermore, since the irradiated body collimator is artificially replaced each time the irradiated body is changed, artificial error should not occur in amounting direction. In this case, since in a state where the mounting bracket is at the imaging position, light is irradiated toward the irradiated body through the opening portion of the irradiated body collimator from the light source section with the irradiation axis of the charged particle beam as the center, the shape of the shadow of light which reaches the irradiated body becomes a shape similar to the opening portion of the irradiated body collimator. Accordingly, by comparing the shape of the shadow of the light with the shape of the irradiation target captured in an image or a photograph in advance, it is possible to reliably perform confirmation of a mounting direction of the irradiated body collimator.

According to an embodiment of the present invention, it is possible to obtain a clear captured image of the opening portion of the multi-leaf collimator. In this way, even if complicated error correction processing or the like is not performed on especially output image data of the imaging section, it becomes possible to confirm whether the shape of the opening portion of the multi-leaf collimator is a shape as planned, with an image.

Hereinafter, a preferred embodiment of a charged particle beam irradiation apparatus according to an embodiment of the present invention will be described in detail referring to the drawings.

Figure 2:
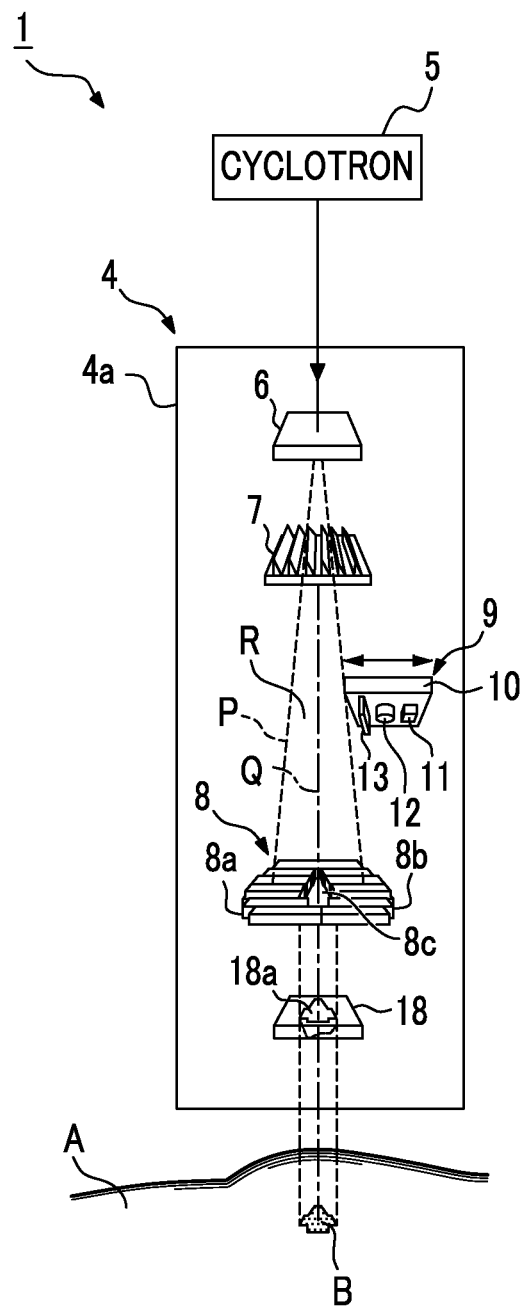
FIG. 2 is a schematic configuration diagram of the charged particle beam therapy apparatus shown in FIG. 1.

FIG. 1 is a perspective view showing a charged particle beam therapy apparatus provided with a charged particle beam irradiation apparatus according to an embodiment of the present invention, and FIG. 2 is a schematic configuration diagram of the charged particle beam therapy apparatus shown in FIG. 1. In each drawing, a charged particle beam therapy apparatus 1 is, for example, an apparatus for performing cancer therapy by irradiating a charged particle beam P with respect to a tumor area (an irradiation target) B that is an affected area in the body of a patient A. As the charged particle beam, for example, a proton beam, a heavy particle beam, or the like can be used.

The charged particle beam therapy apparatus 1 is provided with a rotating gantry 3 provided so as to surround a treatment table 2, and a charged particle beam irradiation apparatus 4 which is mounted on the rotating gantry 3 and can rotate around the treatment table 2 by the rotating gantry 3.

In addition, the charged particle beam therapy apparatus 1 is further provided with a cyclotron (an accelerator) 5. The cyclotron 5 is installed at a position away from the rotating gantry 3 and accelerates and emits a charged particle beam generated at an ion source (not shown). The charged particle beam emitted from the cyclotron 5 is supplied to the charged particle beam irradiation apparatus 4 through a beam transport system (not shown). In addition, it is also possible to rotate the cyclotron 5 integrally with the rotating gantry 3.

The charged particle beam irradiation apparatus 4 has a scatterer 6, a ridge filter 7, a multi-leaf collimator 8, and a patient collimator (an irradiated body collimator) 18 which are disposed in order in an irradiation direction of the charged particle beam P. The scatterer 6, the ridge filter 7, and the multi-leaf collimator 8 are mounted on a casing 4a of the charged particle beam irradiation apparatus 4.

The scatterer 6 is formed of a lead plate or the like and is for expanding the charged particle beam supplied from the cyclotron 5 into a wide beam. The ridge filter 7 is for adjusting dose distribution of the charged particle beam expanded by the scatterer 6. Specifically, the ridge filter 7 imparts a spread-out Bragg peak (SOBP) to the charged particle beam so as to correspond to the thickness (the length in the irradiation direction) of the tumor area B of the patient A. The scatterer 6 and the ridge filter 7 configure an irradiation section which irradiates the charged particle beam P.

The multi-leaf collimator 8 is for setting an irradiation range (an irradiation field) of the charged particle beam P in accordance with the shape of the tumor area B of the patient A. Specifically, the multi-leaf collimator 8 has a pair of leaf groups 8a and 8b which includes a large number of leafs made of, for example, brass. The leaf groups 8a and 8b are disposed so as to face each other. An opening portion 8c through which the charged particle beam P passes is formed between the leaf groups 8a and 8b. The position and the shape of the opening portion 8c can be changed by individually advancing or retreating the leaves of the leaf groups 8a and 8b in a longitudinal direction. In addition, the multi-leaf collimator 8 is used, for example, in a case where the tumor area B of the patient A is large.

The patient collimator 18 is detachably mounted on the casing 4a of the charged particle beam irradiation apparatus 4 on the lower side of the multi-leaf collimator 8. The patient collimator 18 is for setting an irradiation range of the charged particle beam P in accordance with the shape of the tumor area B of the patient A, similar to the multi-leaf collimator 8. The patient collimator 18 is made for each patient A and has an opening portion 18a through which the charged particle beam P passes. The opening portion 18a has dimensions and a shape matching the tumor area B of the patient A. When the multi-leaf collimator 8 is used, the patient collimator 18 is removed from the casing 4a. In addition, when the patient collimator 18 is used, the opening portion 8c of the multi-leaf collimator 8 is more increased than the actual tumor area B.

A collimator shape confirmation unit 9 which can advance and retreat with respect to an irradiation axis Q of the charged particle beam P is disposed between the ridge filter 7 and the multi-leaf collimator 8. The collimator shape confirmation unit 9 is distant from the multi-leaf collimator 8 by, for example, about 400 mm. In addition, the distance between the multi-leaf collimator 8 and a target (the body surface of the patient A) of the charged particle beam P is, for example, about 100 mm.

Figure 3:
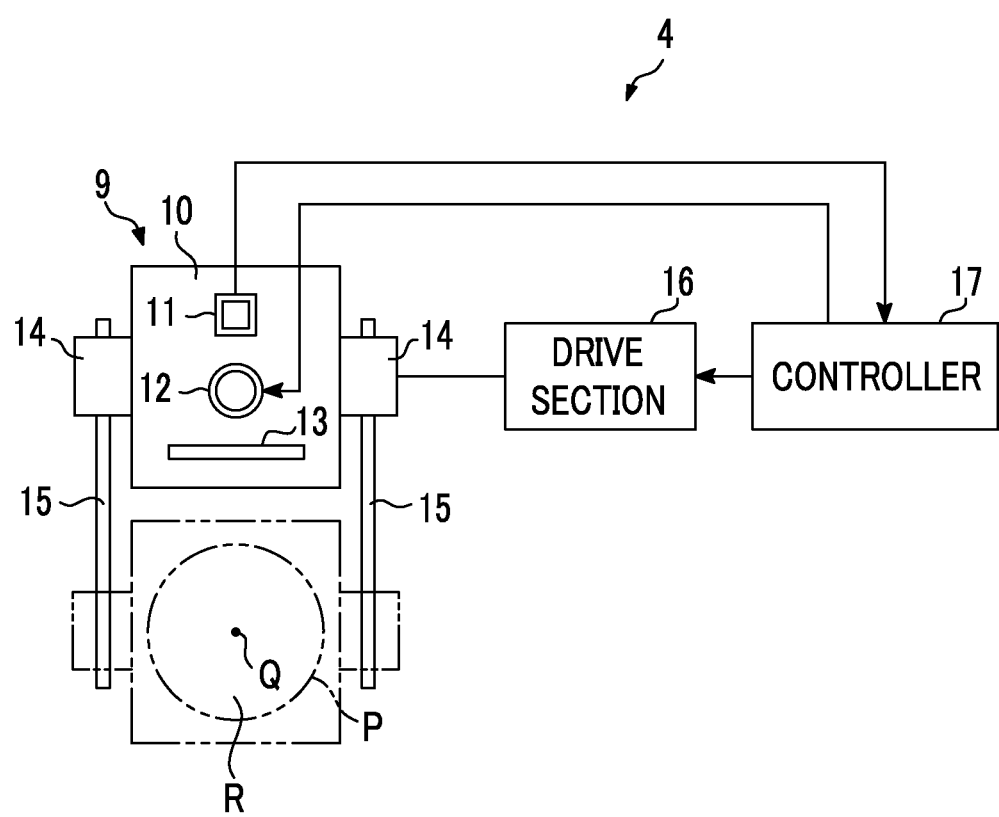
FIG. 3 is a configuration diagram showing a collimator shape confirmation unit shown in FIG. 2, along with a driving control system.

The collimator shape confirmation unit 9 has a flat plate-shaped mounting bracket 10, as shown in FIGS. 2 and 3. In addition, FIG. 3 is a diagram of the collimator shape confirmation unit 9 when viewed from the multi-leaf collimator 8 side. An imaging camera (imaging section) 11 and a projector (a light source section) 12 are mounted adjacently to each other on the back surface of the mounting bracket 10. The imaging camera 11 is configured by, for example, a CCD camera. The imaging camera 11 is for imaging the opening portion 8c of the multi-leaf collimator 8 in order to confirm the shape of the opening portion 8c of the multi-leaf collimator 8.

The projector 12 is configured to have, for example, an LED and irradiates light (visible light, ultraviolet rays, or the like) toward the opening portion 8c of the multi-leaf collimator 8. In this way, when the opening portion 8c of the multi-leaf collimator 8 is imaged by the imaging camera 11, the opening portion 8c is illuminated by the projector 12. Furthermore, if light is irradiated toward the multi-leaf collimator 8 from the projector 12 in a state where the patient collimator 18 is mounted on the casing 4a, the light reaches the body surface of the patient A through the opening portion 8c of the multi-leaf collimator 8 and the opening portion 18a of the patient collimator 18. Accordingly, whether the mounting direction of the patient collimator 18 is right or wrong can be determined by visually confirming the shape of light (shadow) which reaches the body surface of the patient A and also by comparing the shape with a photograph or image data of the tumor area B of the patient A.

Furthermore, a shield wall 13 for protecting the imaging camera 11 and the projector 12 from the charged particle beam P is mounted at a position on the side of the irradiation axis Q of the charged particle beam P with respect to the imaging camera 11 and the projector 12 on the back surface of the mounting bracket 10. The shield wall 13 is formed of a lead plate or the like.

Slide sections 14 are respectively provided at both end portions of the mounting bracket 10. Furthermore, guide rods 15 passing through the slide sections 14 and extending in a direction perpendicular to the irradiation axis Q of the charged particle beam P are respectively disposed on both sides of the mounting bracket 10. The guide rods 15 are fixed to the casing 4a. In this way, the collimator shape confirmation unit 9 can move along each guide rod 15 between an imaging position (refer to a two-dot chain line in FIG. 3) corresponding to an irradiation area R which includes the irradiation axis Q of the charged particle beam P and a retreated position away from the irradiation area R which includes the irradiation axis Q of the charged particle beam P. In addition, usually, the collimator shape confirmation unit 9 is at the retreated position as shown in FIG. 3.

In this case, it is preferable that the projector 12 be mounted on the mounting bracket 10 such that a light outlet of the projector 12 is located on the irradiation axis Q of the charged particle beam P when the collimator shape confirmation unit 9 is at the imaging position, as shown in FIG. 4A. In this way, since the opening portion 8a of the multi-leaf collimator 8 is efficiently illuminated, confirmation of the image of the opening portion 8a by the imaging camera 11 can be accurately performed. Furthermore, since the shape of light which reaches the body surface of the patient A through the opening portion 18a of the patient collimator 18 becomes a shape similar to the opening portion 18a, the patient collimator 18 being correctly mounted on the casing 4a can be confirmed by comparing the shape of the light with the shape of the tumor area B of the patient A captured in an image or a photograph in advance.

Furthermore, in a state where the collimator shape confirmation unit 9 is at the retreated position, as shown in FIG. 4B, the imaging camera 11 is disposed on the side opposite to the irradiation axis Q of the charged particle beam P with respect to the projector 12 and the shield wall 13 is disposed on the side of the irradiation axis Q of the charged particle beam P with respect to the projector 12. In this way, it is possible to sufficiently protect the imaging camera 11 and the projector 12 from the charged particle beam P by the shield wall 13. In addition, the shield wall 13 may have a structure to surround, for example, the imaging camera 11 and the projector 12, or the like, rather than a structure in which the shield wall 13 is disposed closer only to the side of the irradiation axis Q of the charged particle beam P than the projector 12.

In addition, the charged particle beam irradiation apparatus 4 further has a drive section 16 which enables the collimator shape confirmation unit 9 to reciprocate between the retreated position and the imaging position, and a controller 17 connected to the imaging camera 11, the projector 12, and the drive section 16, as shown in FIG. 3.

The drive section 16 is configured to include an air cylinder, an air source, an electromagnetic valve, and the like. In this case, a piston of the air cylinder is connected to the slide section 14 on one side. Furthermore, in addition to this, the drive section 16 may be configured to include a ball screw, an electromagnetic motor, and the like.

The controller 17 controls the projector 12 and the drive section 16 and also determines whether or not the charged particle beam P is irradiated to the tumor area B in the body of the patient A, on the basis of a captured image of the imaging camera 11.

FIG. 5 is a flowchart showing the details of processing procedure which is executed by the controller 17. This processing is used in a case where the patient collimator 18 is not mounted on the casing 4a, and is executed immediately before the charged particle beam P is irradiated to the tumor area B in the body of the patient A.

In FIG. 5, first, the drive section 16 is controlled so as to move the collimator shape confirmation unit 9 from the retreated position to the imaging position (procedure S101). Subsequently, the projector 12 is controlled so as to irradiate light toward the opening portion 8c of the multi-leaf collimator 8 from the projector 12 (procedure S102). Subsequently, an image of the opening portion 8c of the multi-leaf collimator 8 captured by the imaging camera 11 is input (procedure S103).

Subsequently, whether the shape of the opening portion 8c of the multi-leaf collimator 8 is a shape as planned is determined by comparing image data of the opening portion 8c of the multi-leaf collimator 8 with shape data of the opening portion 8c of the multi-leaf collimator 8 planned by a therapy planning device (not shown) (procedure S104).

When it is determined that the shape of the opening portion 8c of the multi-leaf collimator 8 is the shape as planned, determination to carry out irradiation of the charged particle beam P is made (procedure S105) and the result is notified to a main control device (not shown). On the other hand, when it is determined that the shape of the opening portion 8c of the multi-leaf collimator 8 is not the shape as planned, determination not to carry out irradiation of the charged particle beam P is made (procedure S106) and the result is notified to the main control device.

Then, after execution of procedures S105 and S106, the drive section 16 is controlled so as to move the collimator shape confirmation unit 9 from the imaging position to the retreated position (procedure S107).

When the determination to carry out the irradiation of the charged particle beam P is made in procedure S105, thereafter, the charged particle beam P is irradiated to the tumor area B in the body of the patient A. At this time, since the imaging camera 11 and the projector 12 that are susceptible to a radiation are protected from the charged particle beam P by the shield wall 13, the charged particle beam P hardly damages the imaging camera 11 and the projector 12.

As described above, in this embodiment, when the opening portion 8c of the multi-leaf collimator 8 is imaged by the imaging camera 11, the collimator shape confirmation unit 9 having the imaging camera 11 is moved from the retreated position to the imaging position, and therefore, it is not necessary to dispose a half mirror between the multi-leaf collimator 8 and the imaging camera 11 unlike a case where the installation position of the imaging camera 11 is fixed, and the opening portion 8c of the multi-leaf collimator 8 can be directly imaged by the imaging camera 11. For this reason, a problem such as the captured image of the imaging camera 11 being distorted by a half mirror does not arise and it is possible to obtain the captured image in which the contour shape of the opening portion 8c of the multi-leaf collimator 8 is clear.

In this way, since whether or not the contour shape of the opening portion 8c of the multi-leaf collimator 8 is a shape as planned can be correctly confirmed, it becomes possible to effectively search a defect or the like in the multi-leaf collimator 8. Further, since it is not necessary to intricately correct output image data of the imaging camera 11 in order to confirm the contour shape of the opening portion 8c of the multi-leaf collimator 8, complicated image processing or arithmetic processing need not be performed.

In addition, the present invention is not limited to the above-described embodiment. For example, the accelerator is not limited to a cyclotron, but another accelerator (a synchrotron, a synchro-cyclotron, a linac, or the like) may be used. Further, the present invention is not limited to a configuration using a rotating gantry, but a fixed irradiation method may also be adopted in which the charged particle beam irradiation apparatus 4 is fixed with respect to the treatment table 2.

The scatterer 6 and/or the ridge filter 7 is not necessarily required and may be omitted.

The distance between the collimator shape confirmation unit 9 and the multi-leaf collimator 8 is not limited to about 400 mm, but the distance may be different from that. Furthermore, the distance between the multi-leaf collimator 8 and the patient is not limited to about 100 mm, but the distance may be different from that.

The projector 12 is not limited to an LED, and another luminous body (for example, a fluorescent lamp or an incandescent lamp) may be used.

The imaging camera 11 is not limited to a CCD camera, but another camera (for example, CMOS camera) may be used. Further, the present invention is not limited to a configuration in which both the imaging camera 11 and the projector 12 are mounted on the single mounting bracket 10, but a bracket for mounting the imaging camera 11 and another bracket for mounting the projector 12 may be separately provided.

The shield wall 13 is not limited to a configuration in which the shield wall 13 is mounted on the mounting bracket 10, but the shield wall 13 may be mounted on another component (for example, the casing 4a). In short, it is only required for the configuration that the imaging camera 11 and/or the projector 12 can be protected from a radiation when the imaging camera 11 and/or the projector 12 is at the retreated position.

The mounting bracket 10 is not limited to a configuration in which the mounting bracket 10 moves between the imaging position and the retreated position in a linear movement, but a configuration in which the mounting bracket 10 moves while drawing another trajectory (for example, a configuration in which a rotary shaft is mounted on one end of an arm and a bracket is mounted on the other end of the arm) may be used.

The projector 12 is not limited to a configuration in which the light outlet of the projector 12 is located on the irradiation axis Q when the collimator shape confirmation unit 9 is at the imaging position, but the projector 12 may be configured so as not to be located on the irradiation axis Q.

Furthermore, in the above-described embodiments, the mounting bracket 10 on which the imaging camera 11 and the projector 12 are mounted has a flat plate shape. However, the shape of the mounting bracket 10 may be a box shape, a frame shape, or the like.

Furthermore, a configuration is made such that the collimator shape confirmation unit 9 in which the imaging camera 11, the projector 12, and the shield wall 13 are mounted on the mounting bracket 10 can advance and retreat with respect to the irradiation axis Q of the charged particle beam P. However, a configuration may be made such that only the imaging camera 11 can advance and retreat with respect to the irradiation axis Q of the charged particle beam P.

Furthermore, a configuration is made such that whether the shape of the opening portion 8c of the multi-leaf collimator 8 is a shape as planned and whether irradiation of the charged particle beam P is performed are determined by the controller 17. However, the present invention is not particularly limited thereto, but an operator may confirm whether the shape of the opening portion 8c of the multi-leaf collimator 8 is a shape as planned, by viewing the captured image of the opening portion 8c of the multi-leaf collimator 8, and then determining whether the irradiation of the charged particle beam P is performed.

Further, direct imaging as referred to in the above-described embodiments means that imaging is performed without using reflection by a half mirror or the like, and it goes without saying that a sheet or the like can be sandwiched between the multi-leaf collimator 8 and the imaging camera 11 in order to make a captured image clearer.

The embodiment of the present invention can be used in a charged particle beam irradiation apparatus.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation apparatus comprising:
    an irradiation section configured to irradiate an irradiated body with a charged particle beam;
    a multi-leaf collimator configured to set an irradiation range of the charged particle beam which is irradiated from the irradiation section;
    an imaging section that is provided so as to be able to advance and retreat with respect to an irradiation axis of the charged particle beam which is irradiated from the irradiation section, between the irradiation section and the multi-leaf collimator, and directly images an opening portion of the multi-leaf collimator; and
    a drive section configured to move the imaging section between an imaging position corresponding to an irradiation area which includes the irradiation axis of the charged particle beam and a retreated position away from the irradiation area.

2. The charged particle beam irradiation apparatus according to claim 1, wherein the imaging section is mounted on amounting bracket that can advance and retreat with respect to the irradiation axis of the charged particle beam,
    the drive section moves the mounting bracket between the imaging position and the retreated position, and
    a shield wall for protecting the imaging section from the charged particle beam is provided closer to the side of the irradiation axis of the charged particle beam than the imaging section in the mounting bracket when the mounting bracket is at the retreated position.

3. The charged particle beam irradiation apparatus according to claim 2, wherein a light source section configured to irradiate light to the opening portion of the multi-leaf collimator is further mounted on the mounting bracket.

4. The charged particle beam irradiation apparatus according to claim 3, wherein the light source section is mounted on the mounting bracket so as to be located on the irradiation axis of the charged particle beam when the mounting bracket is at the imaging position.

* * * * *